US005705629A

United States Patent [19]
Bhongle

[11] Patent Number: 5,705,629
[45] Date of Patent: Jan. 6, 1998

[54] METHODS FOR H-PHOSPHONATE SYNTHESIS OF MONO- AND OLIGONUCLEOTIDES

[75] Inventor: Nandkumar Bhongle, Shrewsbury, Mass.

[73] Assignee: Hybridon, Inc., Worcester, Mass.

[21] Appl. No.: 546,318

[22] Filed: Oct. 20, 1995

[51] Int. Cl.$^6$ ............................. C07H 1/02; C07H 21/04
[52] U.S. Cl. ........................... 536/25.34; 536/25.3
[58] Field of Search ........................ 536/25.34, 25.3

[56] References Cited

U.S. PATENT DOCUMENTS 4,959,463   9/1990   Froehler et al. .................. 536/25.34

FOREIGN PATENT DOCUMENTS 0219342   4/1987   European Pat. Off. .

OTHER PUBLICATIONS

Agrawal, *Trends in Biotech.* 10, 152 (1992).
Beaucage and Caruthers, *Tetrahedron Lett.* 22, 1859 (1981).
Bhongle and Tang, *Tett. Lett.* 36, 6803 (1995).
Cheng and Petit, *Prog. Biophys. Molec. Biol.* 58, 225 (1992).
Efimov et al., *Nucl. Acids Res.* 21, 5337 (1993).
Froehler et al., *Nucl. Acid. Res.* 14, 5399 (1986).
Froehler, *Methods in Molecular Biology*, vol. 20, Protocols for Oligonucleotides and Analogs, pp. 63–80 (1993).
Gaffney et al., *Tetrahedron Lett.* 29, 2619 (1988).
Garegg et al., *Tetrahedron Lett.* 27, 4055 (1986).
Garegg et al., *Tetrahedron Lett.*, 27, 4051 (1986).
Garegg et al., *Chemica Scripta* 25, 280 (1985).
Garegg et al., *Chemical Scripta* 26, 59 (1986).
Garegg et al., *J. Chem. Soc. Perkin Trans. II*, 1209–1214 (1987).
Gibbs and Larsen, *Synthesis–Stuttgart*, pp. 410–413 (1984).
Hall et al., *J. Chem. Soc.*, 3291 (1957).
Iyer et al., *J. Org. Chem.* 55, 4693 (1990).
Jankowska et al., *Tetrahedron Lett.* 35, 3355 (1994).
Marugg et al., *Tetrahedron Lett.* 27, 2661 (1986).
Pon, "Preparation of Solid Phase Supports," in *Methods in Molecular Biology*, vol. 20, pp. 465–496 (1993).
Sakatsume et al., *Nucleic Acids Res.* 17, 3689 (1989).
Sekine and Hata, *Tetrahedron Lett.* 16, 1711 (1975).
Sekine et al., *Tetrahedron Lett.* 20, 1145 (1979).
Sekine et al., *Tetrahedron Lett.* 29, 1037 (1988).
Stawinski and Thelin, *Nucleosides & Nucleotides* 9, 129 (1990).
Stawinski, "Some Aspects of H–Phosphonate Chemistry," in *Handbook of Organophosphorus Chemistry*, pp. 377–434 (1992).
Uhlmann and Peyman, *Chem. Rev.* 90, 543 (1990).
Stawinski et al., *J. Chem. Soc. Perkin Trans.* 2, 849–853 (1990).
Ishihara, et al., Scandium Trifluoromethanesulfonate as an Extremely Active Acylation Catalyst. *J. Am Chem. Soc.*, 117, 4413–4414 (1995).
Ishihara, et al., Scandium Trifluoromethanesulfonate as an Extremely Active Lewis Acid Catalyst in Acylation of Alcohols with Acid Anhydrides and Mixed Anhydrides. *J. Org. Chem.*, 61, 4560–4567 (1996).

*Primary Examiner*—Gary L. Kunz
*Attorney, Agent, or Firm*—McDonnell Boehnen Hulbert & Berghoff

[57] ABSTRACT

New methods of synthesizing mono- and oligo- nucleotide H-phosphonates are disclosed. The methods comprise contacting a mononucleoside with phosphonic acid and benzoyl anhydride to yield the corresponding mononucleoside H-phosphonate. Preferrably a catalytic amount of triphosgene is also used. A similar procedure can be used to couple a first mononucleoside to a second mononucleoside or to an oligonucleotide, the method comprising contacting, in the presence of benzoic anhydride and, preferrably, a catalytic amount of triphosgene, a mononucleotide or oligonucleotide having a free 5' hydroxyl with a mononucleoside having a 3' hydroxyl-bearing phosphorous moiety (preferably H-phosphonate).

18 Claims, No Drawings

METHODS FOR H-PHOSPHONATE SYNTHESIS OF MONO- AND OLIGONUCLEOTIDES

BACKGROUND OF THE INVENTION

1. Field of the Invention

This invention relates to new methods of synthesizing mononucleoside H-phosphonates and oligonucleotides using the H-phosphonate method.

2. Summary of the Related Art

There has been much interest in recent years in the use of antisense oligonucleotides as instruments for the selective modulation of gene expression in vitro and in vivo. E.g., Agrawal, *Trends in Biotech.* 10, 152 (1992); Chang and Petit, *Prog. Biophys. Molec. Biol.* 58, 225 (1992). Antisense oligonucleotides are constructed to be sufficiently complementary to a target nucleic acid to hybridize with the target under the conditions of interest and inhibit expression of the target. Antisense oligonucleotides may be designed to bind directly to DNA (the so-called "anti-gene" approach) or to mRNA. Id. Expression inhibition is believed to occur by prevention of transcription or translation, or inducement of target mRNA cleavage by RNase H.

Antisense oligonucleotides can be used as a research tool in vitro to determine the biological function of genes and proteins. They provide an easily used alternative to the laborious method of gene mutation (e.g., deletion mutation) to selectively inhibit gene expression. The importance of this method is readily appreciated when one realizes that the elucidation of most known biological processes was determined by deletion mutation.

Antisense oligonucleotides also may be used to treat a variety of pathogenic diseases by inhibiting nucleic acid expression of the pathogen in vivo.

Simple methods for synthesizing and purifying oligonucleotides are now in great demand due to the utility of synthetic oligonucleotides in a wide variety of molecular biological techniques. Initially, the method of choice for synthesizing oligonucleotides was the beta-cyanoethyl phosphoramidite method. Beaucage and Caruthers, *Tetrahedron Lett.* 22, 1859 (1981). In the phosphoramidite procedure, the first nucleotide (monomer 1) is bound by its 3' hydroxyl to a solid matrix while its 5' hydroxyl remains available for binding. The synthesis of the first internucleotide link is carried out by mixing bound monomer 1 with a second nucleotide that has a reactive 3'-diisopropyl phosphoramidite group on its 3' hydroxyl and a blocking group on its 5' hydroxyl (monomer 2). In the presence of a weak acid, coupling of monomer 1 and monomer 2 occurs as a phosphodiester with the phosphorus in a trivalent state. This is oxidized, giving a pentavalent phosphotriester. The protecting group is then removed from monomer 2 and the process is repeated.

The H-phosphonate approach was first reported by Hale et al., *J. Chem. Soc.*, 3291 (1957) and revisited some twenty years later by Sekine and Hata, *Tetrahedron Lett.* 16, 1711 (1975), Sekine et al., *Tetrahedron Lett.* 20, 1145 (1979), Garegg et al., *Chemica Scripta* 25, 280 (1985) ("Garegg I"), and Garegg et al., *Chemica Scripta* 26, 59 (1986) ("Garegg II"). The H-phosphonate method involves condensing the 5' hydroxyl group of the nascent oligonucleotide with a nucleoside having a 3' phosphonate moiety. Once the entire chain is constructed, the phosphite diester linkages are oxidized with t-butyl hydroperoxide or iodine to yield the corresponding phosphotriester. See, e.g., Froehler, "Oligodeoxynucleotide Synthesis," in *Methods in Molecular Biology*, Vol. 20, *Protocols for Oligonucleotides and Analogs*, p. 63–80 (S. Agrawal, Ed., Humana Press 1993) ("Froehler I"); Uhlmann and Peyman, *Chem. Rev.* 90, 543 (1990).

The H-phosphonate approach became practical only with the introduction of pivaloyl chloride as the condensing agent. Sterically hindered carbonyl chlorides such as adamantoyl and pivaloyl chloride (trimethyl acetyl chloride) are typically used as condensing agents. U.S. Pat. No. 4,959,463; European Pat. App. 86307926.5. Since then there have been reports of successful use of this method in both deoxyribonucleotide (Garegg et al., *Tetrahedron Lett.*, 27, 4051 (1986)("Garegg III"); Froehler et al., *Nucl. Acid. Res.* 14, 5399 (1986) ("Froehler II")) and ribonucleotide syntheses (Garegg et al., *Tetrahedron Lett.* 27, 4055 (1986) ("Garegg IV")). See generally Stawinski, "Some Aspects of H-Phosphonate Chemistry," in *Handbook of Organophosphorus Chemistry*, pp. 377–434 (R. Engel, Ed., Marcel Dekker, Inc., New York 1992). The H-phosphonate method offers several advantages over the beta-cyanoethyl phosphoramidite method. The 3' phosphonate monomers are easily prepared and are stable to hydrolysis and oxidation. H-phosphonate chemistry requires no phosphate protecting group because phosphite diester linkages are relatively inert to coupling conditions. Furthermore, the H-phosphonate method requires a shorter cycle time. Finally, a simple reaction can be used to prepare backbone-modified DNA and RNA from the H-phosphonate synthesis product.

The H-phosphonate methods of Froehler I, Garegg III, and Garegg IV, supra, although adequate for small scale synthesis (i.e., less than 1 μmol), are not practical on a large scale (e.g., 10–20 μmol). The main reason is that the methods reported by these groups require 20–30 equivalents of monomer per coupling reaction. At this rate, the monomer consumption costs represent approximately 60% of the oligonucleotide assembly cost.

Gaffney et al., *Tetrahedron Lett.* 29, 2619 (1988), reported an effort to scale up H-phosphonate oligonucleotide synthesis to the 10–20 μmol range while reducing the monomer equivalents consumed per coupling reaction. In synthesizing an 8-mer (consuming 1.53 equivalents of H-phosphonate) and a 26-mer (consuming 5.5 equivalents of H-phosphonate), however, Gaffney's group reported an average coupling yield of only 81% and 87%, respectively. Because of this relatively low coupling efficiency as compared with prior art methods, the authors found it necessary to employ a separate capping step using cyanoethyl H-phosphonate to prevent the elongation of truncated failed sequences in subsequent synthetic cycles. This extra step was necessary because the self-capping efficiency for pivaloyl chloride was found to be too low. According to the method of Gaffney et al., which assumed a 94% coupling yield, the expected result of a 20-mer synthetic reaction would be a crude mixture consisting of 24% product (20-mer) and 76% short chains (e.g., 19-mers, 18-mers, etc.).

Decreased yields are due in large part to some side reactions between the condensing agent and starting material. Efimov et al., *Nucl. Acids Res.* 21, 5337 (1993), demonstrated the use of dipentafluorophenyl carbonate as an activating agent for the H-phosphonate reaction. Use of this compound resulted in a high coupling efficiency with a concomitant decrease in side reactions.

A variety of methods of preparing mononucleoside H-phosphonates have been proposed, including PCl$_3$/azole system (Garegg II, supra; Froehler II, supra), salicylchlorophosphite (Marugg et al., *Tetrahedron Lett.* 27, 2661 (1986)), di- and tri(2,2,2-trifluoroethyl) H-phosphonates (Gibbs and Larsen, *Synthesis-Stuttgart*, pp. 410–413 (1984)), pyro-H-phosphonate (Sakatsume et al., *Nucleic Acids Res.* 17, 3689 (1989)), and transesterification of diphenyl H-phosphonate (Jankowska et al., *Tetrahedron Lett.* 35, 3355 (1994)).

Other methods include oxidative phosphitylation of nucleosides with phosphinic acid in the presence arene sulfonyl derivatives using suitably protected nucleosides. Sekine and Hata, supra. Sekine et al., *Tetrahedron Lett.* 29, 1037 (1988), used phosphonic acid with mesitylenedisulfonyl chloride, but observed a significant side reaction comprising formation of bisnucleoside H-phosphonate diesters. The result was oxidation of the desired H-phosphonate monoesters by the condensing reagent. Garegg et al., *J. Chem. Soc. Perkin Trans. II.*, pp. 1209–1214 (1987). Replacement of sulfonyl chloride with pivaloyl chloride did not reduce this side reaction.

Stawinski and Thelin, *Nucleosides & Nucleotides* 9, 129 (1990), found that they could produce the H-phosphonate monoesters almost exclusively if the phosphonic acid is first converted to pyrophosphonate, which can be done in the presence of the nucleoside and condensing reagent.

Recently, Bhongle reported an improved method of synthesizing mononucleotides and oliognucleotides by the H-phosphonate method using triphosgene to couple phosphonic acid or a 3' phosphonate moiety to a 5'- and base protected mono/oligonucleotide. Bhongle and Tang, *Tett. Lett.* 36, 6803 (1995).

While there has been much interest and work on the development of methods for fast and efficient oligonucleotide synthesis, improved methods are still desirable.

SUMMARY OF THE INVENTION

Disclosed herein is an improved method of synthesizing oligonucleotides by the H-phosphonate approach. In one aspect of the invention, a new method of synthesizing mononucleoside H-phosphonates is disclosed. This method comprises contacting a 5'- and base- protected mononucleoside with phosphonic acid and benzoic anhydride at room temperature. The resulting product is the desired mononucleoside H-phosphonate.

In a preferred embodiment of this aspect of the present invention, a catalytic amount of triphosgene is added to the reaction mixture. The resulting product is the desired mononucleoside H-phosphonate. As is implied, triphosgene accelerates the coupling reaction.

In a second aspect of the invention, a new method of coupling nucleosides is presented. The method comprises contacting a 5'-protected nucleoside or oligonucleotide having a 3' phosphonate moiety with a 3'-protected mononucleoside having a free 5' hydroxyl in the presence of benzoic anhydride. In a preferred embodiment of this aspect of the invention, the coupling reaction is accelerated by the addition of a catalytic amount of triphosgene.

In a third aspect of the invention, a new method of synthesizing oligonucleotide phosphodiesters and phosphorothioates is presented. The method comprises repeated nucleoside coupling according to the first and/or second aspect of the invention followed by oxidation to produce the phosphodiester or oxidative sulfurization to produce the phosphorothioate.

These methods advantageously use benzoic anhydride as an activator of phosphonate coupling. Benzoic anhydride is a stable, inexpensive, commercially available crystalline solid. Like triphosgene, it offers many of the same advantages over prior art activators such as pivaloyl chloride (e.g., safety and stability), but it is about 30 times cheaper than triphosgene. This is the first use of an anhydride as a coupling agent of which we are aware.

The foregoing merely summarizes certain aspects of the present invention and is not intended, nor should it be construed, to limit the invention in any way. All of the patents and other publications recited in this specification are hereby incorporated by reference in their entirety.

DETAILED DESCRIPTION OF THE PREFERRED EMBODIMENTS

The present invention generally comprises new methods for synthesizing nucleotide monomers useful for constructing oligonucleotides by the H-phosphonate method, as well as methods for constructing oligonucleotides.

In a first aspect of the invention, a new method is provided for the synthesis of nucleoside H-phosphonate monomers. The method comprises contacting a mononucleoside having a 3' hydroxyl moiety with benzoic anhydride and an excess of phosphonic acid ($H_3PO_3$). As an example, one can use 10 eq. of phosphonic acid and 5 eq. of benzoic anhydride per eq. of mononucleoside. The reaction product is the desired mononucleoside H-phosphonate. Preferably, the mononucleoside is suitably protected, for example, at the 5' position (e.g., with DMT) and, if necessary, at the base.

As used herein, the terms "suitable" and "suitably," when used to describe a general class of compounds, methods, or techniques (as the case may be) that serves a desired function means any compound, method, or technique of that class that does not cause or induce undesirable side effects that would either defeat the purpose for which the compound, method, or technique is used, or, on balance, outweigh the benefits of using the particular compound, method, or technique. For example, as used herein, a "suitable solvent" is any solvent that is capable of dissolving the starting materials, permits the reaction to proceed, and does not itself chemically react with the starting or ending materials. A suitable protecting group is one that prevents reaction at the site to which it is bound and that can be cleaved, if cleavage is desired, without altering the molecule that it protects. The term "protecting group" as used herein encompasses not only moieties traditionally used to prevent side reactions at the site to which it is bound (e.g., DMT or an acetyl moiety), but also any other chemical moiety (such as a mono- or oligonucleotide) that effects a protecting group type function. For example, the 3' most N-1 nucleotides of a N-mer oligonucleotide will serve as a 3' protecting group for the 5' nucleotide of the N-mer. For convenience, as used herein the term "oligonucleotide" refers to any nucleic acid chain comprising at least two nucleotides and that can be chemically synthesized.

In a preferred embodiment of this aspect of the invention, a catalytic amount of triphosgene is added to accelerate the coupling reaction. As used herein, a "catalytic amount" of triphosgene means an amount that is about 10–15 times less than the amount of benzoic anhydride used. In this embodiment the reaction is slightly exothermic on a small scale. Care should be taken, therefore, in large scale preparations.

In a second aspect of the present invention, a new method is provided for the synthesis of dinucleotides. This method comprises contacting, in the presence of benzoic anhydride, a first mononucleoside having a 3' H-phosphonate with a second mononucleoside having a free 5' hydroxyl. The result is a dinucleoside H-phosphonate. Preferably, the first mononucleoside is suitably protected, for example, at the 5'-O position (e.g., by DMT) and, if necessary, at the base, and the second mononucleoside is suitably protected at the 3'-O (e.g., by an acetyl moiety) and, if necessary, the base. Any suitable solvent may be used. In a preferred embodiment, a catalytic amount of triphosgene is added to accelerate the reaction.

In a third aspect of the present invention, a new method is provided for the synthesis of oligonucleotides. This method comprises contacting, in the presence of benzoic anhydride, a nascent oligonucleotide having a free 5' hydroxyl moiety with a mono- or oligo- nucleotide having a 3' H-phosphonate moiety to yield an oligonucleotide H-phosphonate that is one or more nucleotide(s) greater in length (depending on whether a mono- or oligo- nucleotide was used). The resulting oligonucleotide can then be treated with additional nucleotides (mono- or oligo-) in the presence of benzoic anhydride to further increase its length. This procedure is repeated until the desired oligonucleotide sequence has been synthesized. The nascent oligonucleotide can be of any conveniently synthesized length and is preferably anchored to a solid support. Preferably, the oligonucleotide is suitably protected, for example, at its 3' end (e.g., by the solid support) and, if necessary, at the bases, and the mono- or oligo- nucleotide is suitably protected at the 5'-O end (e.g., by DMT) and, if necessary the base or bases. In a preferred embodiment, a catalytic amount of triphosgene is added to accelerate the reaction.

In this aspect of the invention, the method of synthesizing an oligonucleotide comprises sequentially:

(a) contacting a nascent mono- or oligo- nucleotide having a free 5' hydroxyl moiety with a 5' protected mono- or oligo- nucleotide having a free 3' H-phosphonate moiety in a reaction mixture containing benzoic anhydride to produce a nascent oligonucleotide bearing a 5' protecting group;

(b) cleaving the protecting group from the previously produced 5' protected nascent oligonucleotide to produce a nascent oligonucleotide having a free 5' hydroxyl moiety;

(c) optionally contacting the previously produced nascent oligonucleotide having a free 5' hydroxyl moiety with a 5' protected mono- or oligo- nucleotide having a free 3' H-phosphonate moiety to produce a 5' protected nascent oligonucleotide;

(d) optionally repeating (b) and (c) sequentially until an oligonucleotide of the desired sequence is obtained;

(e) oxidizing the oligonucleotide of (d) to yield a phosphodiester or phosphorothioate.

In the foregoing method, the reaction mixture generally comprises one or more suitable solvents.

In a preferred embodiment of the third aspect of the invention, a solid support is loaded with mononucleoside. Many such methods are known to those skilled in the art. E.g., Pon, "Preparation of Solid Phase Supports," in *Methods in Molecular Biology*, vol. 20, pp. 465–496 (S. Agrawal, Ed., Humana Press, Totawa N.J. 1993) and references cited therein. The desired oligonucleotide is incrementally synthesized by the foregoing method by the addition of mononucleotides or di- or tri- nucleotide building blocks. Preferably, the desired oligonucleotide is synthesized in increments of one nucleotide at a time.

Oligonucleotides synthesized according to either the second or third aspects of the invention may be subjected to oxidation with, for example, iodine to yield an oligonucleotide in which the H-phosphonate internucleoside linkages are converted to phosphodiesters. Froehler, id. at 63–80. Alternatively, the oligonucleotide H-phosphonate may be subjected to oxidative sulfurization (e.g., Iyer et al., *J. Org. Chem.* 55, 4693 (1990)) to yield an oligonucleotide in which the H-phosphonate internucleoside linkages have been converted to phosphorothioates.

The methods according to the invention are advantageously used with either ribo- or deoxyribo- mononucleosides and oligonucleotides. Ribonucleotides will have to be protected at the 2'-O position. In order to prevent unwanted side reactions in any of the foregoing aspects of the invention, the benzoic anhydride activator is preferably added to a mixture of the reactants and, if it is to be used, the triphosgene catalyst added subsequent to the benzoic anhydride.

The following examples are offered for illustrative purposes only and are not intended, nor should they be construed, to limit the invention in any way.

EXAMPLES

Example 1

Synthesis of DMT-Protected Thymidine H-Phosphonate with Benzoic Anhydride Activator 5'-O-dimethoxytritylthymidine (Chem Empex Int'l, Wooddale, Ill.) was contacted with phosphonic acid (Aldrich, Milwaukee, Wis.) (10 eq.) and benzoic anhydride (3.33 eq.) (Aldrich, Milwaukee, Wis.) in a pyridine/acetonitrile solvent. The H-phosphonate monomer product was observed. After 16 hours at room temperature, in addition to the product, TLC analysis indicated the presenece of starting material. Neither the addition of dimethylaminopyridine, tributylphosphine, or scandium triflate as catalysts affected the course of the reaction. It was discovered, however, that a catalytic mount of triphosgene (Aldrich, Milwaukee, Wis.) accelerated the reaction, resulting in nearly complete reaction after 8 hours. Only trace amounts of starting mononucleoside were detected by TLC. Significantly, no 3'-O-benzoyl derivative of the 5'-O-dimethoxytritylthymidine was observed, clearly indicating that benzoic anhydride acts as an activator of phosphonic acid. Only very minute amounts of product were observed in the absence of benzoic anhydride.

Example 2

Synthesis of DMT-Protected Thymidine H-Phosphonate with Benzoic Anhydride Activator and Triphosgene Catalyst A solution of triphosgene (0.050 g, 0.17 mmol) in acetonitrile (Burdick Jackson, Muskegon, Mich.) (0.5 ml) was added dropwise to a solution of phosphonic acid (0.376 g, 4.58 mmol), 5'-O-dimethoxytritylthymidine (0.25 g, 0.46 mmol) and benzoic anhydride (0.519 g, 2.29 mmol) in 8 ml of acetonitrile/pyridine (Burdick Jackson, Muskegon, Mich.) (1:1) solvent. The reaction mixture was stirred at room temperature for 8 hours. It was then poured into 50 ml of 1M triethylammonium bicarbonate (TEAB) (made by reacting triethylamine (Aldrich, Milwaukee, Wis.) with dry ice in aqueous medium) buffer, concentrated under reduced pressure, and extracted with methylene chloride (EM Science, Gibbstown, N.J.) (3×20 ml). The combined organic layer was dried over $Na_2SO_4$ (Em Science, Gibbstown, N.J.), and methylene chloride was evaporated under reduced pressure to give a colorless foam. Silica gel chromatography of the crude product yielded pure H-phosphonate (0.288 g, 88.3% yield).

Table 1 displays the data from synthesizing four different mononucleotide H-phosphonates by the foregoing protocol. All yields correspond to isolated pure compounds. The reaction conditions were not optimized. $^{31}$P NMR of the crude products confirmed the H-phosphonate product structures. TLC of the pure products was identical to the commercially available materials.

TABLE 1

| Base | % Yield |
|---|---|
| (thymine structure) | 88.3 |
| (N4-benzoyl cytosine structure) | 81.2 |
| (N6-benzoyl adenine structure) | 90.0 |
| (N2-isobutyryl guanine structure) | 76.7 |

Example 3

Synthesis of a Nucleotide Dimer Using the Benzoic Anhydride Method

Add triphosgene (0.2–0.3 eq.) to a stirred solution of a nucleoside H-phosphonate (1.0 eq), 3' protected nucleoside (1.2 eq.) and benzoic anhydride (2.0–3.0 eq.) in pyridine. When TLC indicates that the reaction is over (6–12 hr), add 2M TEAB. The reaction is concentrated in vacuo and the residue partitioned between methylene chloride and 0.5M TEAB. The organic layer is separated. The aqueous layer is extracted with methylene chloride. The combined organic layer is dried (Na$_2$SO$_4$) and evaporated in vacuo to give crude nucleotide dimer.

Example 4

Synthesis of an Oligonucleotide

In an automated synthesizer the following cycle is follwed for the H-phosphonate approach:

1. Wash A
   The resin is washed with acetonitrile several times.
2. Deblock
   The DMT goup on the first base is removed by 2.5% dichloroacetic acid in dichloromethane. Multiple hits of short time are preferred to give a good reaction.
3. Wash A
   The resin is washed with acetonitrile several times.
4. Wash B
   The resin is washed with pyridine/acetonitrile several times.
5. Coupling reaction
   Nucleoside H-phosphonate (2–3 eq. solution in pyridine/acetonitrile), benzoic anhydride (6–9 eq. solution in pyridine/acetonitrile), triphosgene (0.6–0.9 eq. solution in acetonitrle) are added to the reaction vessel sequentially.
6. Wash B
   The resin is washed with pyridine/acetonitrile several times.
7. Repeat 1–6 until sequence is complete
8. Oxidation
   An I$_2$ solution or sulfur solution is used to oxidize the H-phosphonate linkages to phosphate (PO or PS) linkages. This reaction can be performed in a round bottom flask and, therefore, need not be conducted in an automated synthesizer.

I claim:

1. A method of synthesizing a mononucleoside H-phosphonate comprising contacting a mononucleoside having a free 3' hydroxyl moiety with phosphonic acid and benzoic anhydride in a reaction mixture.

2. The method according to claim 1, further comprising adding a catalytic amount of triphosgene to the reaction mixture.

3. A method of synthesizing a dinucleotide comprising contacting a mononucleoside having hydroxyl-bearing phosphorous moiety at the 3' position with a mononucleoside having a free 5' hydroxyl group in the presence of benzoic anhydride in a reaction mixture.

4. The method according to claim 3, further comprising adding a catalytic amount of triphosgene to the reaction mixture.

5. The method according to claim 3 wherein the hydroxyl-bearing phosphorous moiety is H-phosphonate.

6. The method according to claim 4 wherein the hydroxyl-bearing phosphorous moiety is H-phosphonate.

7. A method of coupling a first mono- or oligo- nucleotide to a second mono- or oligo- nucleotide comprising contacting a first mono- or oligo- nucleotide having a hydroxyl-bearing phosphorous moiety at the 3' position with a second mono- or oligo- nucleotide having a free 5' hydroxyl group in the presence of benzoic anhydride in a reaction mixture.

8. The method according to claim 7, further comprising added a catalytic amount of triphosgene to the reaction mixture.

9. The method according to claim 7 wherein the hydroxyl-bearing phosphorous moiety is H-phosphonate.

10. The method according to claim 8 wherein the hydroxyl-bearing phosphorous moiety is H-phosphonate.

11. The method of claim 7 wherein the first and second nucleotides are mononucleotides.

12. The method of claim 8 wherein the first and second nucleotides are mononucleotides.

13. The method of claim 7 wherein the first nucleotide is a mononucleotide and the second nucleotide is a solid support-bound oligonucleotide.

14. The method of claim 8 wherein the first nucleotide is a mononucleotide and the second nucleotide is a solid support-bound oligonucleotide.

15. A method of synthesizing an oligonucleotide comprising sequentially:

(a) contacting a nascent mono- or oligo- nucleotide having a free 5' hydroxyl moiety with a 5' protected monoor oligo- nucleotide having a free 3' H-phosphonate moiety in a reaction mixture containing benzoic anhydride to produce a nascent oligonucleotide bearing a 5' protecting group;

(b) cleaving the protecting group from the previously produced 5' protected nascent oligonucleotide to produce a nascent oligonucleotide having a free 5' hydroxyl moiety;

(c) optionally contacting the previously produced nascent oligonucleotide having a free 5' hydroxyl moiety with a 5' protected mono- or oligo- nucleotide having a free 3' H-phosphonate moiety to produce a 5' protected nascent oligonucleotide;

(d) optionally repeating (b) and (c) sequentially until an oligonucleotide of the desired sequence is obtained;

(e) oxidizing the oligonucleotide of (d) to yield a phosphodiester or phosphorothioate.

16. The method of claim 13 further comprising adding a catalytic amount of triphosgene to the reaction mixture in (a), (c), or both.

17. The method of claim 14 wherein the free 3' hydroxyl-bearing phosphorous moiety is H-phosphonate.

18. The method according to claim 15 wherein the nascent oligonucleotide is incrementally increased in length by one nucleotide at a time.

* * * * *